United States Patent
Marini et al.

(10) Patent No.: US 9,808,654 B2
(45) Date of Patent: Nov. 7, 2017

(54) POST PROCEDURE SKIN CARE GEL AND METHODS OF USE THEREOF

(71) Applicant: JAN MARINI SKIN RESEARCH, San Jose, CA (US)

(72) Inventors: Jan Marini, San Jose, CA (US); Subhash J. Saxena, Ringoes, NJ (US)

(73) Assignee: JAN MARINI SKIN RESEARCH, San Jose, CA (US)

( * ) Notice: Subject to any disclaimer, the term of this patent is extended or adjusted under 35 U.S.C. 154(b) by 157 days.

(21) Appl. No.: 13/764,456

(22) Filed: Feb. 11, 2013

(65) Prior Publication Data

US 2014/0228291 A1    Aug. 14, 2014

(51) Int. Cl.
| | |
|---|---|
| A61K 8/00 | (2006.01) |
| A61K 31/74 | (2006.01) |
| A61K 38/18 | (2006.01) |
| A61Q 19/00 | (2006.01) |
| A61K 8/64 | (2006.01) |
| A61K 8/58 | (2006.01) |
| A61K 8/891 | (2006.01) |
| A61K 8/98 | (2006.01) |
| A61K 8/04 | (2006.01) |

(52) U.S. Cl.
CPC .............. *A61Q 19/00* (2013.01); *A61K 8/042* (2013.01); *A61K 8/585* (2013.01); *A61K 8/64* (2013.01); *A61K 8/891* (2013.01); *A61K 8/981* (2013.01)

(58) Field of Classification Search
USPC ........................... 424/59, 401; 514/18.6, 18.8
See application file for complete search history.

(56) References Cited

U.S. PATENT DOCUMENTS

| | | | |
|---|---|---|---|
| 4,297,276 A | 10/1981 | Goldstein et al. | |
| 5,789,542 A | 8/1998 | McLaughlin et al. | |
| 5,853,755 A | 12/1998 | Foldvari et al. | |
| 5,955,343 A | 9/1999 | Holmes et al. | |
| 6,328,987 B1 | 12/2001 | Marini et al. | |
| 6,602,519 B1 | 8/2003 | Stevenson et al. | |
| 6,821,524 B2 | 11/2004 | Marini | |
| 8,318,678 B2 | 11/2012 | Marini | |
| 2002/0049422 A1 | 4/2002 | Brewitt et al. | |
| 2003/0147823 A1 | 8/2003 | Woodward et al. | |
| 2004/0052760 A1 | 3/2004 | Michelet et al. | |
| 2004/0132667 A1* | 7/2004 | Lintner ........................... 514/18 | |
| 2007/0020220 A1 | 1/2007 | Osborne et al. | |
| 2007/0166267 A1 | 7/2007 | Majewski et al. | |
| 2007/0196318 A1 | 8/2007 | Marini | |
| 2009/0214607 A1* | 8/2009 | Lintner ................... A61K 8/35 424/401 | |
| 2009/0263513 A1 | 10/2009 | Marini | |
| 2010/0247693 A1 | 9/2010 | Marini | |
| 2011/0009374 A1* | 1/2011 | Keller .......................... 514/179 | |
| 2012/0288478 A1* | 11/2012 | Florence et al. ............. 424/93.1 | |
| 2013/0189211 A1 | 7/2013 | Marini | |
| 2014/0066837 A1* | 3/2014 | Moy ............................... 604/22 | |

FOREIGN PATENT DOCUMENTS

| | | |
|---|---|---|
| CA | 2230389 | 10/1999 |
| EP | 1203579 A1 | 5/2002 |
| EP | 1369107 A1 | 12/2003 |
| EP | 1825845 A1 | 8/2007 |
| WO | 94/04184 | 3/1994 |
| WO | 99/32072 | 7/1999 |
| WO | 99/49883 | 10/1999 |
| WO | 00/06190 | 2/2000 |
| WO | 02/36143 | 5/2002 |
| WO | 2005/048968 | 6/2005 |
| WO | WO 2006-048339 A2 * | 5/2006 |
| WO | 2007/143006 | 12/2007 |
| WO | 2009/148551 A1 | 12/2009 |
| WO | 2009/148947 | 12/2009 |

OTHER PUBLICATIONS

Shimabukuro et al. Fibroblast growth factor-2 regulates the synthesis of hyaluronan by human periodontal ligament cells. Abstract, vol. 203, No. 3, pp. 557-563 (Jun. 2005).*
Foldvari; et al. "Palmitoyl Derivatives of Interferon α: Potential for Cutaneous Delivery", Journal of Pharmaceutical Sciences (1998), 87(10):1203-1208.
Foldvari; et al. "Dermal and transdermal delivery of protein pharmaceuticals:lipid-based delivery systems for interferon α", Biotechnol Appl Biochem (1999), 30:129-137.
"*Homo sapiens* vascular endothelial growth factor", Genbank, accession No. NM_003376, downloaded Oct. 15, 20012, 4 pgs.
"Human mRNA for transforming growth factor-beta (TGF-beta)", Genbank, accession No. X02812 J05114, downloaded Oct. 15, 2002, 2 pgs.
Knighton; et al. "Wound healing Angiogenesis: Indirect Stimulation by Basic Fibroblast Growth Factor", The Journal of Trauma (Dec. 1990), 30:S134-144.
Malinda; et al. "Thymosin β4 Accelerates Wound Healing", J Invest Dermatol (Sep. 1999), 113(3):364-368.

(Continued)

*Primary Examiner* — Elizabeth C Kemmerer
*Assistant Examiner* — Regina M Deberry
(74) *Attorney, Agent, or Firm* — Pamela J. Sherwood; Bozicevic, Field & Francis LLP

(57) ABSTRACT

Compositions and methods are provided for a post-procedure care following the treatment of skin with cosmetic skin resurfacing treatments, which include without limitation a variety of laser treatments, chemical peeling and dermabrasion, by applying a silicone-based gel formulation in combination with therapeutic peptides. Peptides of interest include one or more of transforming growth factor, epidermal growth factor, and basic fibroblast growth factor. The formulation may further comprise an effective dose of one or more acylated peptides, which peptides are active in remodeling of the skin.

12 Claims, No Drawings

(56) References Cited

OTHER PUBLICATIONS

"Marini Lash Eyelash Conditioner", Skin-Etc.com, downloaded May 4, 2007, http://www.skin-etc.com/janmaageiney.html.
Roberts; et al. "Increased microvascular permeability and endothelial fenestration induced by vascular endothelial growth factor", J Cell Sci (Jun. 1995), 108(Pt6):2369-2379.
Sasaki; et al. "Influence of prostaglandin F2α and its analogues on hair regrowth and follicular melanogenisis in a murine model", Exp Dermatol (May 2005), 14(5):323-328.
Wolf; et al. "Prostaglandin analogs for hair growth: Great expectations", Dermatol Online J (Aug. 2003), 9(3):7.

\* cited by examiner

POST PROCEDURE SKIN CARE GEL AND METHODS OF USE THEREOF

BACKGROUND OF THE INVENTION

The skin is the largest organ, constitutes one of the largest surface areas, and accounts for about 15 percent of the entire weight of the human body. The skin is composed of several layers, the two main layers of which are the epidermis and dermis. The dermis lies below the epidermis and is comprised of loose connective tissues such as collagen, elastin and reticular fibers. The dermis includes a number of pores and structures such as blood vessels, nerves, hair, follicles, smooth muscles, glands and lymphatic tissues. Removing the top layers of the dermis promotes regeneration of collagen, elastine, and epidermis. This can rejuvenate the facial skin long term, and improve the appearance of fine line and wrinkles. Skin resurfacing can also remove superficial blemishes such as the brown spots of ageing, dilated capillaries, and small keratoses.

One procedure currently in wide use for skin resurfacing involves exposure to a laser, usually one that employs nonablative laser technology. Because any given laser emits light of only one wavelength (or color), they work in cosmetic applications through a process called selective photothermolysis. To be effective, the wavelength of the light beam must be in sync with the color of the target which is to be addressed, whether that be brown spots, unsightly red broken capillaries or some other undesirable skin condition. The most-commonly used lasers for the treatment of pigmented lesions, such as sun spots, age spots melasma and other forms of hyperpigmentation are the pulsed dye, Nd:YAG and fractional (Fraxel) lasers, along with nonlaser, light-based treatments, such as IPL.

Lasers useful in cosmetic procedures also include $CO_2$ (carbon dioxide) laser or Erbium YAG for treating lines and wrinkles, the removal of warts and skin tags, acne scars and for cutting skin in laser-assisted surgery. Pulsed Dye Lasers have also shown some success, along with less aggressive nonlaser, light-based treatments, such as intense pulsed light (IPL) and LED photofacials. Most cosmetic laser procedures provide some level of superficial tightening because they produce a controlled injury of the skin, which encourages increased collagen production. For more significant tightening results $CO_2$ lasers or nonlaser, light-based treatments, such as Titan infrared devices and Thermage radio-frequency based systems may be used.

Resurfacing methods also include chemical peeling and dermabrasion. A chemical peel causes a chemical burn. Dermabrasion mechanically removes the epidermis and a variable layer of dermis. Recently, a rapid scanning device has been added to the cutting laser, enabling a predictable depth of skin to be destroyed. Resurfacing methods treat superficial wrinkles and repair skin aged by light.

Despite the large numbers of such procedures, there remains a need for materials, methods and systems for treating and dressing post-procedure skin. It is desirable to accelerate the healing and to restore the functional barrier property of the skin as rapidly as possible, preferably with a cosmetically acceptable formulation. Skin resurfacing procedures result in predictable post-operative sequelae including facial edema, wound exudate and erythema. In addition, there may be pain, pruritis, hyperpigmentation, milia formation and acne. It is desirable to address all of these consequences of wounding and aspects of healing.

SUMMARY OF THE INVENTION

Compositions and methods are provided for a post-procedure silicone-based gel formulation, which formulation comprises one or a mixture of cyclic siloxanes, which may be a defined mixture of specific length siloxanes, e.g. cyclotetrasiloxane, cyclopentasiloxane, cyclohexasiloxane, cycloheptasiloxane, etc. in combination with therapeutic peptides. Peptides of interest include one or more of transforming growth factor, epidermal growth factor, and basic fibroblast growth factor. In some embodiments all three therapeutic peptides are present. The formulation may further comprise an effective dose of one or more acylated peptides, which peptides are active in remodeling of the skin. In some embodiments the formulation is substantially free of petrolatum.

Methods are provided for post-procedure care following the treatment of skin with cosmetic skin resurfacing treatments, which include without limitation a variety of laser treatments, chemical peeling and dermabrasion. The formulations of the invention are applied topically to the skin post-procedure. The formulations may be applied within about 1 hour after completion of the procedure, about 4 hours post-procedure, about 6 hours post-procedure, usually applied within about one day, and reapplied as needed throughout the time needed for healing, for example from about 3, 5, 7, 10 or more days.

In addition to the healing benefits provided by the formulations of the invention, in which the length of time required for the appearance of the skin recover is shortened, the formulation of the invention provides a cosmetically acceptable formulation, thereby allowing continued use over an extended period of time for healing.

DETAILED DESCRIPTION OF THE EMBODIMENTS

Cosmetic skin resurfacing treatments can have a negative short term effect on the epidermis, including erythema, dry skin, inflammation, and/or post-inflammatory hyperpigmentation (PIH). Another significant disadvantage relates to the post-treatment recovery period. For example, it may require up to several weeks or even months to fully recover and to allow the skin the form a new epidermal layer. During a period ranging from a few weeks to several weeks after a deep resurfacing treatment, the new skin is usually bright pink or red. The skin may also be more sensitive.

The compositions of the present invention can help alleviate the impact of these cosmetic procedures and decrease the time for recovery of the skin. The non-aqueous silicone based gel formulation is cosmetically acceptable, and provides for improved barrier and healing properties.

DEFINITIONS AND COMPOSITIONS

Cyclic siloxanes (for example n=4-7) are cyclic dimethyl polysiloxane compounds. Cyclomethicone is a mixture, while cyclotetrasiloxane (n=4), cyclopentasiloxane (n=5), cyclohexasiloxane (n=6), and cycloheptasiloxane (n=7) have a defined chain length. For a review, see Johnson et al., Cosmetic Ingredient Review.

Of particular interest is cyclopentasiloxane (decamethylcyclopentasiloxane) and cyclohexasiloxane:

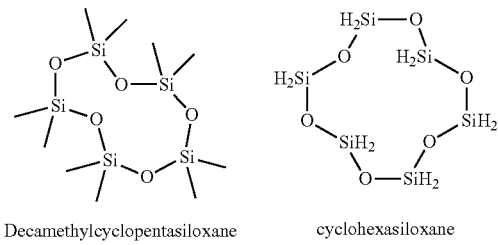

Decamethylcyclopentasiloxane     cyclohexasiloxane

The compositions of the invention are primarily silicone based, and will usually comprise from about 80% to about 95%, usually from about 85% to about 90% of the total volume as one or a combination of cyclic dimethyl polysiloxanes. In some embodiments the composition of the invention comprises cyclopentasiloxane at a concentration of from about 60% to about 85%, usually from about 65% to about 80%; and cyclohexasiloxane at a concentration of from about 1% to about 25%, usually at a concentration of from about 5% to about 15%. The formulation may be free of petrolatum.

Transforming growth factor beta 1 (TGFβ1) (INCI:rh-Polypeptide-22) is a multifunctional peptide that controls proliferation, differentiation, and other functions in many cell types. Many cells synthesize TGFβ1 and almost all of them have specific receptors for this peptide. The effect of TGFβ1 on wound healing angiogenesis has been explored by Knighton et al. (1990) *J. Trauma* 30:S134-144. The polypeptide sequence of human TGFβ1 and corresponding genetic sequence may be found in Genbank, accession number X02812 J05114, Derynck et al. (1985) Nature 316 (6030), 701-705. Recombinant human TGFβ1 is commercially available, e.g. from Caregen Co., Ltd. In the compositions of the present invention TGFβ1 is used at a concentration of at least about 500 pg/ml, usually at least about 100 ng/ml, more usually at least about 1 µg/ml, and not more than about 1 mg/ml, usually not more than about 100 µg/ml, and may be used at a concentration of from about 1 µg/ml to about 50 µg/ml, or at about 20 µg/ml.

Epidermal growth factor (EGF) (INCI:sh-Oligopeptide-1) is a low-molecular-weight polypeptide hormone that results in cellular proliferation, differentiation, and survival, found predominantly in the duodenum and in the salivary glands. The polypeptide sequence of human EGF and corresponding genetic sequence may be found in Genbank, accession number NG_011441. Recombinant EGF is commercially available at, for example, Caregen Co., Ltd., BD Biosciences; R and S Pharmchem; etc. In the compositions of the present invention EGF is used at a concentration of at least about 500 pg/ml, usually at least about 100 ng/ml, more usually at least about 1 µg/ml, and not more than about 1 mg/ml, usually not more than about 100 µg/ml, and may be used at a concentration of from about 1 µg/ml to about 50 µg/ml, or at about 20 µg/ml.

Fibroblast Growth Factor 2 ((3-FGF, FGF) (INCI:sh-Polypeptide-1) is a wide-spectrum mitogenic, angiogenic, and neurotrophic factor that is expressed at low levels in many tissues and cell types and reaches high concentrations in brain and pituitary. FGF2 has been implicated in a multitude of physiologic and pathologic processes, including limb development, angiogenesis, wound healing, and tumor growth. The polypeptide and corresponding genetic sequence of human FGF may be found in Genbank, accession number NM_002006. In the compositions of the present invention FGF is used at a concentration of at least about 250 pg/ml, usually at least about 50 ng/ml, more usually at least about 0.5 µg/ml, and not more than about 0.5 mg/ml, usually not more than about 50 µg/ml, and may be used at a concentration of from about 0.5 µg/ml to about 25 µg/ml, or at about 10 µg/ml.

Peptides, including but not limited to, di-, tri-, tetra-, and pentapeptides, as well as oligo-peptides of from about 3 to about 10 amino acids in length and derivatives thereof, comprising at least one lipid moiety, which moiety may be myristoyl, palmitoyl, etc., may be included in compositions of the present invention in amounts that are safe and effective. The formulation comprises an effective dose of one or more such acylated peptides, which peptides are active in remodeling of the skin.

Peptides of particular interest stimulate macromolecules of the dermis, e.g. fibronectin, collagen, and the like. The stimulatory activity of the peptides provides for an improved activity in enhancing the appearance of the skin. In some embodiments, the acylated peptide is a palmitoylated peptide (e.g., palmitoyl tetrapeptide-7, palmitoyl oligopeptide, etc.) The commercially available blend Matrixyl® 3000 from Sederma Corporation may be used, for example comprising an association of 2 palmitoylated matrikines: Palmitoyl-Gly-His-Lys and [SEQ ID NO:1] Palmitoyl-Gly-Glu-Pro-Arg, see WO 2005/048968, herein specifically incorporated by reference.

The peptide agents of the present invention are formulated at an effective concentration within the subject cosmetic compositions, meaning at a concentration that provides the intended benefit when applied topically. An effective concentration of peptide or peptide-like compounds is preferably in a range of at least about 0.5%, more usually at least about 1.0%, at least about 2.5%, usually less than about 10% by weight, or less than about 5%. Conveniently the acylated peptides are provided by Matrixyl® 3000 at a concentration of from about 0.05% to about 15%, usually from about 1% to about 10%, more usually from about 3% to about 5%, e.g. about 3%.

For use in the present invention these proteins variants and active fragments of these proteins, as known in the art, may be used. The proteins may be produced from eukaryotic or prokaryotic cells by recombinant methods, isolated from cells in a native form, or may be synthesized in vitro as known in the art.

The compositions of the invention may optionally comprise other skin benefit materials. These include estradiol; progesterone; pregnanalone; coenzyme Q10 (ubiquinone); methylsolanomethane (MSM); copper peptide (copper extract); plankton extract (phytosome); kojic acid; ascorbyl palmitate; PEG-100, sodium hyaluronate; sodium oleate, glycine soja, etc. The skin benefit materials may be present in total at concentrations of from about 1% to about 15%, usually from about 1% to about 5%.

The compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen may also be used. The exact amount of sunscreen employed in the compositions can vary depending upon the degree of protection desired from the sun's UV radiation.

The compositions of the invention include a cosmetically acceptable vehicle to act as a diluent, dispersant or carrier for the extracts, so as to facilitate its distribution and uptake when the composition is applied to the skin. As discussed above, the compositions of the invention are a non-aqueous silicone-based gel, and the compositions usually comprise from about 80% to about 95%, usually from about 85% to about 90% of the total volume as one or a combination of cyclic dimethyl polysiloxanes.

After inclusion of the peptides, as discussed above, and other skin benefit materials as discussed above, the vehicle may comprise other vehicle ingredients as appropriate to provide a cosmetically desirable effect. The non-silicone vehicle ingredients may be present in total at a concentration of from about 1% to about 15%, usually from about 5% to about 15%, or from about 10% to about 15%. Additional ingredients of interest include emollients, buffers, surfactants, preservatives, thickeners, moisturizers, wetting agents, and the like.

The surfactants can be present, alone or in a mixture, in an amount of from about 0.5% to about 8% by weight, usually about 1.5% to 2.5%, or around 2%. Nonionic surfactants, amphoteric surfactants, zwitterionic surfactants and anionic surfactants are generally suitable, including without limitation polysorbate 20. Suitable anionic surfactants include, e.g. alkaline or alkaline earth salts, alpha-olefin sulfonates, sulfosuccinates, disodium laureth-3 sulfosuccinate, disodium PEG-5 lauryl citrate sulfosuccinate, disodium ricinolamido MEA-sulfosuccinate or disodium laurylamido MEA-sulfosuccinate and alkyl ether carboxylates.

Suitable nonionic surfactants include e.g. alkoxylated fatty alcohols, alkoxylated fatty acid esters, alkoxylated partial glycerides, saturated or unsaturated fatty acids, alkoxylated polyol esters, and alkylpolyglucosides, such as coconut glucosides, lauryl glycosides or decylglucosides. For example, carylyl glycol, hexylene glycol, butylene glycol, ethoxylated lauryl alcohol, tetradecyl alcohol, cetyl alcohol, oleyl alcohol or stearyl alcohol, which are used alone or in mixtures with each other, as well as fatty alcohols of ethoxylated lanolin, are suitable as fatty alcohol ethoxylates. Furthermore the ethoxylated fatty acid sugar esters known as nonionic surfactants, especially ethoxylated sorbitan fatty acid ester, are suitable for use in the cosmetic preparations according to the invention. The suitable ethoxylated fatty acid sugar esters include those marketed under the trade names Tween™ and Arlacel™ by ICI surfactants and the alkyl-polyglycosides, which are marketed under the trade names Plantaren™ or Plantacare™ by Henkel or under the trade name Oramix™ by Seppic.

Suitable amphoteric surfactants include for example betaines, such as cocoamidopropylbetaine or lauryl betaine, sulfobetaines, such as cocoamidopropyl hydroxysultaine, glycinates, such as cocoamphoglycinate (INCI-name: sodium cocoamphoacetate) and diglycinates and propionates, such as cocoampho-propionate.

The compositions of the invention may also contain additives and adjuvants which are conventional in the cosmetic, pharmaceutical or dermatological field, such as hydrophilic or lipophilic gelling agents, buffers e.g. aminomethyl propanol; hydrophilic or lipophilic active agents, preservatives (e.g., chlorhexidine, phenoxyethanol, EDTA, potassium sorbate, etc.), antioxidants, solvents, fragrances, thickeners, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Antioxidants include, without limitation, ubiquinone, and may be included at a concentration of from about 0% to about 5%, usually less than about 2%, and may be around 1% by weight.

Exemplary oils which may be used according to this invention include mineral oils (liquid petrolatum), plant oils (liquid fraction of karite butter, sunflower oil), animal oils (perhydrosqualen(e), synthetic oils (purcellin oil), and fluoro oils (perfluoropolyethers). Fatty alcohols, fatty acids (stearic acid) and waxes (paraffin wax, carnauba wax and beeswax) may also be used as fats.

Emulsifiers which may be used include but are not limited to steareth-20, glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers (e.g., methyl methacrylate/glycol dimethacrylate crosspolymer), polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

Emollients and moisturizers are usually included at a combined concentration of from about 1% to about 10%, from about 2.5% to about 7.5%, or at about 6%. Of interest are included petrolatum, sodium hyaluronate, PEG-100 stearate, ethylhexyl glycerin, glycerin, butylene glycol, and the like. An emollient may be present to provide a water-in-oil emulsion. In some embodiments petrolatum is included at a concentration of from about 1% to about 25%, usually less than about 20%, less than about 10%, or less than or at about 5%.

Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate. In some embodiments, the ester is an alkyl benzoate, such as a long chain alkyl ester, where the alkyl group may be saturated or unsaturated and branched or linear. In some embodiments, the alkyl benzoate is a $C_{12}$-$C_{15}$ alkyl benzoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0 to 5% by weight, preferably from about 0.5% to 2% by weight of the composition, or at about 1%. Exemplary thickeners are carbomer, cross-linked polyacrylate materials available under the trademark Carbopol. Gums may be employed such as xanthan, carrageenan, gelatin, karaya, pectin and locust beans gum.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

In certain embodiments, a composition of the invention includes a combination of peptides, particularly $TGF\beta1$, EGF and FGF; acylated peptides, in a cosmetically acceptable non-aqueous silicone-based gel. The subject composition may include additional agents or additives that are not in themselves active agents but play a role in promoting the usefulness or effectiveness of an active agent and in providing a cosmetically acceptable vehicle.

Compositions of the invention may be applied to any subject and used to treat a variety of skin conditions that result from cosmetic skin resurfacing, including laser treatments, dermabrasion and chemical peels. A typical composition of the invention includes aminolevulinic acid, an acylated peptide and a cosmetically acceptable vehicle formulated as a solution, lotion, cream, gel, ointment, liniment, solvent, emulsion, dispersion, hydrodispersion, aerosol, propellant, soap, exfoliant or transdermal patch, which may be applied topically to the skin so as to treat, prevent, wash, condition or otherwise effect a condition of the skin.

Cosmetic Skin Resurfacing Procedures

Recently various methods have been developed for removing superficial skin layers to cause the growth of new skin layers (i.e., commonly described as skin resurfacing treatment, or cosmetic skin resurfacing treatment) and are used for cosmetic purposes, such as generating tighter, younger looking skin, treating wrinkles, hyperpigmentation, and other skin blemishes or irregularities. In some embodiments the compositions of the invention can be applied to the skin following a burn, e.g. a sunburn, and the like.

Following the removal of surface skin layers at a particular depth, the body's natural wound-healing response begins to regenerate the epidermis and underlying wounded skin layers. The range of resurfacing treatments can vary on the depth of the skin removal and wound. Techniques for skin layer removal, such as deep resurfacing treatments (e.g., $CO_2$ laser treatments or ruby laser treatments), extend well into the reticular dermis and may cause significant growth of new skin layers. Other laser resurfacing techniques may include Erbium laser resurfacing. Other techniques include mechanical dermabrasion using high-speed abrasive wheels.

Fractional laser resurfacing or fractional thermolysis treats a fraction of the skin, and is of interest for post-procedure treatment with the compositions of the invention. Only specific areas are targeted using lights that are delivered in small, closely spaced micro beams. Both the epidermis and dermis are penetrated. Only a small proportion of the skin receives the laser light, while the other zones in between are left intact. This way, the skin heals much faster because only fractional damage was caused by the heat of the light source. The micro injured cells start the process of healing with collagen remodeling. The healthy unaffected tissues help to fill in the damaged area with new cells. Areas of affected tissue that extend through the epidermis into the dermis. These areas can be either "non-ablative" (the laser beams coagulate the affected tissue) or "ablative" (the laser beams vaporize the affected tissue).

Chemical peels may also be used and range from a superficial to a deep resurfacing treatment, depending on the treatment parameters. Superficial exfoliation, peel or abrasion removes some or all of the epidermis. Popular superficial chemical peeling agents include α-hydroxy acids, e.g., glycolic acid or other "fruit acids" such as citric and lactic acids; trichloroacetic acid; resorcinol and Jessner's solution. Medium depth peels penetrate to the papillary dermis and typically use 40-50% trichloroacetic acid as the chemical peeling agent. Deep peels penetrate to the reticular dermis and typically use phenol as the chemical peeling agent.

Other cosmetic procedures for skin treatment include radiofrequency therapy. Energy and heat through radiofrequency is applied to skin thereby heating the epidermis and underlying tissue, which tightens the skin by heating the underlying collagen and causing it to contract.

Plasma energy is a method used for treatment of skin conditions including, but not limited to, facial and non-facial rhytides, superficial skin lesions, actinic keratosis, seborrhoeic keratosis, and viral papillomata. Plasma is a gas in which atoms have been ionized or stripped of electrons. The thermal energy from the plasma is thought to be absorbed by the skin, creating growth conditions for new collagen and skin regeneration for a natural, more youthful appearance. By delivering plasma energy deep into the dermis, new epidermis emerges as the old surface epidermis begins to shed.

Photofacials are a series of full face, gentle pulsed light treatments that may improve the appearance of sun damaged and aged skin, as well as reduce facial and neck redness and flushing.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. Sites for resurfacing techniques include various regions of skin, particularly the face, hands, sites of birthmarks, undesirable spider veins, warts, and the like. The compositions of the invention can be applied within one day of a resurfacing procedure, and may be applied with 12 hours, within 6 hours, within one hour of a resurfacing procedure, as directed by a medical practitioner. Reapplication is desirable as required, and treatment may continue for one day, three days, 5 days, 7 days, 10 days, 14 days or more.

The cosmetic composition of the invention can be formulated in any form suitable for application to the site of interest, typically as a gel. The composition can be packaged in any suitable container to suit its viscosity and intended use by the consumer. For example packaged in a bottle, or a propellant-driven aerosol device or a container fitted with a pump suitable for finger operation. When the composition is a gel, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Palmitate conjugate
<220> FEATURE:
<223> OTHER INFORMATION: Synethic sequence

<400> SEQUENCE: 1

Gly Glu Pro Arg
 1
```

EXAMPLE

Example 1 illustrates a post-procedure topical composition according to the present invention. The composition can be processed in conventional manner. The composition is suitable for cosmetic use. In particular the composition is suitable for topical application to a site of interest following a burn or other skin resurfacing procedure.

| Post-Procedure Gel | |
|---|---|
| Cyclopoentasiloxane | 70% |
| Cyclohexasilicone | 15% |
| Matrixyl ™ 3000* | 3% |
| Transforming growth factor (INCI: rh-Polypeptide-22) | 0.00002% |
| Epidermal Growth Factor (INCI: sh-Oligopeptide-1) | 0.00002% |
| Fibroblast Growth Factor (INCI: sh-polypeptide-1) | 0.00001% |
| emollients | 6% |
| surfactants | 2% |
| antioxidants | 1% |
| thickeners | 2% |

*Matrixyl ™ 1 3000 INCI: Glycerin (and) Water (and) Butylene Glycol (and) Carbomer (and) Polysorbate 20 (and) Palmitoyl Oligopeptide (and) Palmitoyl Tetrapeptide-7.

What is claimed is:

1. A method for post-procedure treatment following a skin resurfacing procedure, comprising:
   topically applying to the skin of the subject following the skin resurfacing procedure from 1 to 100 ml. of a silicone-based gel comprising:
   from 85% to 95% of the total volume cyclic dimethyl polysiloxane;
   Transforming growth Factor (TGFβ1) at a concentration of from 1 to 50 μg/ml; Epidermal Growth Factor (EGF) at a concentration of from 1 to 50 μg/ml; and Basic Fibroblast Growth Factor (FGF) at a concentration of from 0.5 to 25 μg/ml;
   Palmitoyl-Gly-His-Lys and SEQ ID NO: 1 Palmitoyl-Gly-Glu-Pro-Arg at a concentration of from 0.5% to 5% by weight;
   in a cosmetically acceptable vehicle.

2. The method of claim 1, wherein the cyclic dimethyl polysiloxane is a mixture of cyclopentasiloxane and cyclohexasiloxane.

3. The method of claim 2, wherein cyclopentasiloxane is present at a concentration of 60% to 85% of the total volume.

4. The method of claim 3, wherein cyclohexasiloxane is present at a concentration of from 1% to 25% of the total volume.

5. The method of claim 1, wherein the gel further comprises petrolatum at a concentration of from 1 to 25% by weight.

6. The method of claim 5, wherein petrolatum is present at a concentration of from 1% to less than 5% by weight.

7. The method of claim 1, wherein the skin resurfacing procedure is selected from chemical peeling, laser skin resurfacing, hair removal using chemicals or light energy, vein removal, microdermabrasion, plasma energy treatment, skin treatment using light energy, and photofacial.

8. The method of claim 7, wherein the post-procedure treatment is maintained for at least 10 days.

9. The method of claim 1, wherein the silicone-based gel is applied within 6 hours following the skin-resurfacing procedure.

10. The method of claim 1, wherein the silicone-based gel is free of petrolatum.

11. A method for post-procedure treatment following a facial skin resurfacing procedure, comprising:
- topically applying to the facial skin of the subject within 6 hours of the skin resurfacing procedure from 1 to 100 ml. of a silicone-based gel comprising:
- from 60% to 85% of the total volume cyclopentasiloxane and 1-25% of the total volume cyclohexasiloxane;
- TGFβ1 at a concentration of from 1 to 50 μg/ml; EGF at a concentration of from 1 to 50 μg/ml; and FGF at a concentration of from 0.5 to 25 μg/ml;
- Palmitoyl-Gly-His-Lys and SEQ ID NO: 1 Palmitoyl-Gly-Glu-Pro-Arg at a concentration of from 0.5% to 5% by weight;
- in a cosmetically acceptable vehicle.

12. The method of claim 11, wherein the silicone-based gel is free of petrolatum.

* * * * *